United States Patent [19]

Wang et al.

[11] Patent Number: 5,194,673

[45] Date of Patent: Mar. 16, 1993

[54] PROCESS OF ALKOXY AND ARYLOXY ISOTHIOCYANATE PREPARATION

[75] Inventors: Samuel S. Wang, New Haven; Lino G. Magliocco, Fairfield, both of Conn.

[73] Assignee: American Cyanamid Company, Stamford, Conn.

[21] Appl. No.: 923,765

[22] Filed: Jul. 27, 1992

[51] Int. Cl.$^5$ ............................................. C07C 125/04
[52] U.S. Cl. .................................... 560/137; 560/148
[58] Field of Search ............................. 560/137, 148

[56] References Cited

U.S. PATENT DOCUMENTS 4,778,921 10/1988 Lewellyn et al. .................. 560/137

*Primary Examiner*—Johann Richter
*Attorney, Agent, or Firm*—Frank M. Van Riet

[57] ABSTRACT

Alkoxy and aryloxy isothiocyanates are produced by the reaction of a haloformate and an alkali or alkaline earth metal thiocyanate in the presence of water and (i) a catalyst comprising a six membered mononuclear or ten membered fused polynuclear aromatic, heterocyclic compound having 1 or 2 nitrogen atoms as the only hetero atoms in the ring and (ii) a co-catalyst comprising an alkali metal or alkaline earth metal salt of an acid having a pKa of about $10^{-3}$ or below. The co-catalyst accelerates the reaction rate, increases product purity and reduces the adverse effects of impurities in certain grades of the thiocyanate reactants.

11 Claims, No Drawings

PROCESS OF ALKOXY AND ARYLOXY ISOTHIOCYANATE PREPARATION

BACKGROUND OF THE INVENTION

Alkoxy and aryloxy isothiocyanates are well-known versatile, organic intermediates which, by virtue of highly reactive multifunctionalities, can undergo a variety of condensation and cyclization reactions. For instance, Heilbron et al, J. Chem. Soc. 1948, 1340, made use of the ready addition of alkoxycarbonyl isothiocyanate to alpha-aminonitrites in their synthesis related to penicillin and purines. Other useful organic syntheses based on alkoxy and aryloxy isocyanates are set forth by Esmail et al., Synthesis, 301, (1975).

Ethoxycarbonyl isothiocyanate was first prepared by R. E. Doran in 1896 by reacting lead thiocyanate with ethylchloroformate in boiling toluene with relatively poor yields, J. Chem. Soc. 69, 324 (1896). In 1908, Dixon and Taylor reported, J. Chem. Soc. 93, 684 (1908), that methylchloroformate, ethylchloroformate, benzylchloroformate, phenyl chloroformate and o- and p-tolylchloroformate, were reacted with potassium thiocyanate in boiling acetone to form the corresponding isothiocyanate.

One of the reasons for low yields in Dixon et al's method was confirmed by Takamizawa et al to be the simultaneous formation of an unreactive thiocyanate isomer. With ethylchloroformate, two isomers were obtained in about 30% yields while with butylchloroformate the yields were 34% for the isothiocyanate and 21% for the thiocyanate isomer. Yields of 31% for the isothiocyanate and 3.5% for the thiocyanate isomer were obtained with allylchloroformate, it being postulated that the formation of the two isomers was due to the existence of the mesomeric thiocyanate ion and isothiocyanate ion both of which can effect the nucleophilic attack on the carbonyl carbon and cause the thiocyanate and isothiocyanate isomer product. Later workers improved reaction conditions to favor the isothiocyanate formation by adding catalytic amounts of triethylamine and longer reaction times; Goerdeler et al, Chem Ber. 104, 1606 (1971). The use of acetonitrile and ethyl acetate as solvents was reported by Lamon; J. Heterocyclic Chem., 5, 837 (1968); Goerdeler et al, Chem. Ber. 96, 526, (1963). Yields, however, were only up to about 60%. Anders et al, Ger. Pat. No. 1215144, 66, reported the preparation of alkoxy and aryloxy isothiocyanates using silyl isothiocyanate while Goerdeler et al, Chem. Ber. 98, 2954 (1965) disclosed the pyrolysis of thiozolinediones as a means for producing them, see also Schenk, Chem. Ber. 99, 1258 (1966).

In a later publication, Chem. Ber. 116, 2044, (1983), Goerdeler et al reported the use of an aromatic heterocyclic nitrogen catalyst such as pyridine in carbon tetrachloride for the preparation of alkoxythiocarbonyl isothiocyanate, however, the yield was only 52%. Using the propoxy analog, Goerdeler et al obtained only a 13% yield of the corresponding isothiocyanate.

The production of phenoxycarbonyl isothiocyanate is also taught by Babu; J. Heterocyclic Chem. 20, 1127, (1983). Thus, the prior art methods for preparing alkoxy and aryloxy isothiocyanates are ineffective in terms of yields and the formation of the undesirable thiocyanate isomer. Additionally, the use of organic solvents creates costly removal problems and poses serious air emission hazards.

In Lewellyn et al., commonly-assigned U.S. Pat. No. 4,778,921, is described a procedure for the formation of alkoxy and aryloxy isothiocyanates whereby the desired products are obtained in higher yields and purity than when the aforementioned prior art techniques are employed. The process of the Lewellyn et al. invention eliminates the use of organic solvents, and furthermore, since the by-product is alkali metal halide, waste disposal is facilitated.

The Lewellyn et al. process depends on the synthesis of the alkoxy and aryloxyisothiocyanates in an all aqueous medium; it being completely unexpected that such a medium could be employed since both the starting material, i.e., the alkyl or arylhaloformate and product isothiocyanate are normally water-reactive. The use of the aqueous medium was made possible because of the conjoint use therewith of a catalyst comprising a six membered mononuclear or a ten membered fused polynuclear aromatic, heterocyclic compound having 1 or 2 nitrogen atoms as the only hetero atoms in the ring. The unique combination of catalyst and the aqueous medium unexpectedly allowed isothiocyanate formation in high yields and purity. Furthermore, the product isothiocyanate, a strong lachrymator, although isolatable, was not required to be isolated, i.e. it could be reacted in situ with other compounds, e.g., alcohols, amines, mercaptans, etc., to produce many useful derivatives, such as promoters, as is well known to those skilled in this art.

It has now been discovered that the Lewellyn et al. process can be rendered even more useful if an effective amount of a co-catalyst is added to the reaction mixture. Such co-catalysts, comprising salts of alkali metals and alkaline earth metals of weak acids, such as, by way of typical example, sodium acetate, sodium borate, sodium phosphate, sodium carbonate, and the like, have been found to accelerate the rate of formation to the respective alkoxy or aryloxy carbonyl isothiocyanates and to overcome the deleterious effects of impurities, such as thiourea, often encountered in commercial alkali metal and alkaline earth metal thiocyanate solutions. As will be shown hereinafter, judicious selection of the co-catalysts is required because, unexpectedly, compounds such as ammonium salts and quaternary ammonium salts have a decidedly adverse effect.

DESCRIPTION OF THE INVENTION INCLUDING PREFERRED EMBODIMENTS

The present invention relates to a process for the production of an alkoxy or aryloxy isothiocyanate which comprises contacting a haloformate having the formula

wherein R is an alkyl radical, preferably a $C_1$-$C_8$ alkyl radical, an alkene radical, preferably a $C_2$-$C_4$ radical, or an aryl radical, preferably a $C_6$-$C_{10}$ aryl radical, and X is a halogen, with an alkali or alkaline earth metal thiocyanate under an appropriate rate of addition of haloformate such as to prevent a run-away reaction, in the presence of water, (i) from about 0.1% to about 10.0% by weight, based on the weight of haloformate, of a catalyst comprising a six membered mononuclear or ten membered fused polynuclear aromatic, heterocyclic compound having 1 or 2 nitrogen atoms as the only hetero atoms in the ring; and (ii) from about 0.1% to about 15.0% by weight, based on the weight of thiocyanate of a co-catalyst comprising an alkali metal or alkaline earth metal salt of an acid having a pKa of about $10^{-3}$ or below, and at a temperature ranging from about $-10°$ C. to about 40° C. for up to about 16 hours.

In preferred embodiments, the invention contemplates such a process wherein R is an ethyl or a phenyl radical; the haloformate is ethyl chloroformate; the alkali metal thiocyanate is sodium thiocyanate; the catalyst comprises a pyridine or a quinoline compound unsubstituted in the 2-position; particularly, pyridine or quinoline. Preferred processes are those wherein the co-catalyst is a sodium or potassium salt of a substituted or unsubstituted saturated or unsaturated carboxylic acid, a substituted or unsubstituted aromatic acid, carbonic acid, boric acid, phosphoric acid, or a mixture of any of the foregoing; especially processes wherein the co-catalyst is selected from sodium acetate, sodium phosphate, sodium borate, sodium carbonate, or a mixture of any of the foregoing. Special mention is made of the process as above-defined wherein R is ethyl, X is chlorine, the alkali metal thiocyanate is sodium thiocyanate, the catalyst is quinoline, and the co-catalyst is sodium acetate.

The reaction proceeds according to the equation:

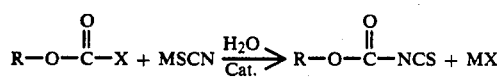

wherein M is an alkali or alkaline earth metal and R and X are as described above.

Both starting materials used in the process of the present invention are well known and any method for their preparation can be used. The alkali or alkaline earth metal thiocyanate may be formed by the reaction of alkali or alkaline earth metal cyanide with sulfur in the presence of a phase transfer catalyst such as a quaternary ammonium salt, see U.S. Pat. No. 4,482,500. It has been found that commercial alkali metal isothiocyanate solutions commonly contain impurities, such as thiourea and ammonium isothiocyanates. Such impurities have been found to have an uncommonly adverse effect on the reaction rate and to cause deposition of heavy precipitates during the reaction. Such problems are readily overcome with the use of the co-catalysts disclosed herein.

In following the process of the present invention, an equimolar equivalent of the alkoxy or aryloxy haloformate is carefully added to an aqueous solution of the alkali or alkaline earth metal thiocyanate in the presence of the catalyst and co-catalyst under the above temperature conditions. A preferred temperature range is 5°-15° C. A preferred catalyst concentration is 0.5 to 5.0%, by weight, based on the weight of haloformate used. A preferred co-catalyst concentration is 0.1 to 5.0%, same basis.

Useful haloformates include the methoxy, ethoxy, isopropoxy, n-butoxy, isobutoxy, amyloxy, hexyloxy, 2-ethylhexyloxy, benzoxy, phenoxy, o- or p-tolyloxy, allyloxy etc, chloro, bromo, iodo, etc., formates.

The catalysts employed in the novel process of the present invention include pyridine, or quinoline, pyrimidine, pyrazine, quinoxaline and the like and substituted derivatives thereof such as their alkyl, halo, nitrite, alkoxy, etc., substituted derivatives. Any derivative may be used except those substituted in the 2-position.

The co-catalysts employed in the novel process of the present invention include sodium, potassium, lithium, calcium, magnesium, barium, and the like, salts of saturated and unsaturated carboxylic acids, such as formic, acetic, acrylic, methacrylic, butyric, valeric, hexanoic, heptanoic, octanoic, palmitic, stearic, oleic, linoleic, halo- or cyano-substituted carboxylic acids such as chloroacetic acid or cyanoacetic acid, and aromatic acids such as benzoic acid or naphthoic acids and the corresponding halo or cyano or nitro substituted aromatic acids may be used. Also useful are salts of carbonic acid, phosphoric acid, boric acid, and the like. The catalyst and the co-catalyst can each comprise mixtures of any of the compounds described.

The reaction is conveniently monitored by gas chromatography, whereby samples of the organic layer are periodically withdrawn from the reaction flask and injected into the GC instrument for the disappearance of the haloformate and the appearance of the corresponding isothiocyanate. The reaction time can proceed for up to 16 hours and can vary from one to two hours or eight to ten hours depending on the reaction temperatures, the amount of the catalyst and the concentration of the aqueous alkali or alkaline earth metal thiocyanate. The resultant isothiocyanates can be isolated from the reaction mixture by the addition of sufficient amount of water to dissolve the alkali or alkaline earth metal halide salt and the organic layer separated from the aqueous salt layer by virtue of lower density. Besides GC, the individual isothiocyanate may be characterized by IR, NMR and boiling point. The infrared spectrum of the isothiocyanate includes absorption bands at 1960-1990 cm$^{-1}$ for the N=C=S group, together with peaks at 1750 cm$^{-1}$ and at 1220-1260 cm$^{-1}$ for the C—O group in the alkoxy or aryloxy moiety of the molecule. Boiling points of recovered exemplary isothiocyanates are essentially the same as those reported in the literature. They are given below:

| PRODUCT | b.p./torr |
|---|---|
| Methoxycarbonyl isothiocyanate | 30° C./12 |
| Ethoxycarbonyl isothiocyanate | 26° C./1.8 |
| Butoxycarbonyl isothiocyanate | 60° C./6 |
| Phenoxycarbonyl isothiocyanate | 87° C./27 |

The following examples are set forth for purposes of illustration only and are not to be construed as limitations on the present invention except as set forth in the appended claims. All parts and percentages are by weight unless otherwise specified.

EXAMPLE 1

To 162 parts of a 50% aqueous solution of sodium thiocyanate are added 4.37 parts of refined grade quinoline. The reaction mixture is cooled to 10° C. under constant agitation, and ethyl chloroformate 110 parts, is carefully introduced to the reaction mixture through a calibrated addition funnel in 10 minutes. The reaction temperature is kept at 10° C. throughout the procedure with ice water cooling. Samples of organic layer are withdrawn hourly from the reaction flask and inspected with the GC instrument for the disappearance of the ethyl chloroformate and the appearance of the ethoxycarbonyl isothiocyanate. For the purpose of comparison, the reaction time is defined as the time required for the ethyl chloroformate content to decrease to 2%. Using this procedure and an impurity-free reagent grade of sodium thiocyanate and adding sodium acetate as a co-catalyst in an amount of 2.98 parts/162 parts of 50% sodium thiocyanate, the reaction time is 5.0 hours and no precipitate is formed. If no sodium acetate is added as co-catalyst, the reaction time increases to 6.0 hours and a slight precipitate is formed.

To test the utility of a given additive, the foregoing procedure is repeated, but a weighed amount of the given additive is added as part of the 50% sodium thiocyanate solution. The procedure is conducted under the identical conditions using the same lot of quinoline and ethyl chloroformate. In addition to the reaction time, the amount of formation of a precipitate which as been identified as the quinolinium thiocyanate complex salt, an undesirable impurity, is monitored at the end of each reaction. The additives used and the results obtained are set forth in Table I:

COMPARATIVE EXAMPLE NOS. 3A*, 3B*, and 3C*

These three procedures show the adverse effects of $NH_4SCN$ on reaction rate. Even in small concentrations, the rate is decreased and the reaction time is increased to 8.25 and 9.0 hours at the 0.36 and 0.72 part levels. Furthermore, when NaSCN is completely replaced with $NH_4SCN$, the reaction is extremely slow (>24 hrs).

COMPARATIVE EXAMPLE NOS. 3D*, 3E*, 3F*

These three procedures demonstrate the adverse effects of a phase transfer catalyst such as tetrabutylammonium bromide (TBAB). The reaction time increases and moderate to heavy precipitate formation is observed.

COMPARATIVE EXAMPLE NOS. 3G* and 3H*

These two procedures show the adverse effects of

TABLE I
PREPARATION OF ETHOXYCARBONYL ISOTHIOCYANATE BY REACTING SODIUM THIOCYANATE AND ETHYL CHLOROFORMATE

| Example | NaSCN Grade | Impurities in NaSCN | Additive Tested parts/162 parts of 50% NaSCN | Reaction Time | Precipitate Formation |
|---|---|---|---|---|---|
| 1A* | Reagent | None | None | 6.0 hrs. | slight |
| 1 | Reagent | None | NaOAc, 2.89 | 5.0 hrs. | none |
| 2 | Reagent | None | NaOAc, 5.6 | 5.0 hrs. | none |
| 3A* | Reagent | None | $NH_4SCN$, 0.36 | 8.25 hrs. | light |
| 3B* | Reagent | None | $NH_4SCN$, 0.72 | 9.0 hrs. | moderate |
| 3C* | $NH_4SCN$ | None | None | >24 hrs. | heavy |
| 3D* | Reagent | None | TBAB**, 0.2 | 7.5 hrs. | moderate |
| 3E* | Reagent | None | TBAB**, 0.4 | 7.5 hrs. | moderate |
| 3F* | Reagent | None | TBAB**, 0.8 | 9.0 hrs. | heavy |
| 3G* | Reagent | None | Thiourea, 0.37 | 9.5 hrs. | heavy |
| 3H* | Reagent | None | Thiourea, 0.74 | 11 hrs. | heavy |
| 3I* | Industrial Grade A | 0.22% TU*** 0.25% $NH_4SCN$ | None | 9.5 hrs. | heavy |
| 3 | Industrial Grade A | 0.22% TU*** 0.25% $NH_4SCN$ | NaOAc, 2.8 | 8.0 hrs. | moderate |
| 4A* | Industrial Grade B | 0.22% TU*** 0.09% $NH_4SCN$ | None | 9.5 hrs. | heavy |
| 4 | Industrial Grade B | 0.22% TU*** 0.09% $NH_4SCN$ | NaOAc, 2.8 | 7.5 hrs. | moderate |
| 5A* | Industrial Grade C | 0.25% TU 0.08% $NH_4SCN$ | None | 9.5 hrs. | heavy |
| 5 | Industrial Grade C | 0.25% TU 0.08% $NH_4SCN$ | NaOAC, 2.8 | 7.25 hrs. | moderate |
| 6A* | Industrial Grade D | 0.215% TU 0.019% $NH_4SCN$ | None | 10.0 hrs. | heavy |
| 6 | Industrial Grade D | 0.215% TU 0.019% $NH_4SCN$ | NaOAc, 2.8 | 8.0 hrs. | moderate |
| 7 | Industrial Grade B | 0.22% TU 0.09% $NH_4SCN$ | $Na_3PO_4 \cdot 12H_2O$, 4.6 | 5.0 hrs. | slight |
| 8 | Industrial Grade B | 0.22% TU 0.029% $NH_4SCN$ | $Na_2B_2O_7 \cdot 10H_2O$, 6.5 | 5.0 hrs. | slight |
| 9 | Industrial Grade B | 0.22% TU 0.029% $NH_4SCN$ | $Na_2CO_3$, 1.8 | 5.0 hrs. | slight |

*Comparative Example
**Tetrabutylammonium bromide
***Thiourea

The data in Table I show the following:

COMPARATIVE EXAMPLE NO. 1A*

This is the control experiment using Reagent grade NaSCN which contains no impurities. The reaction time observed is 6 hours.

EXAMPLE NOS. 1 amd 2

These two runs (in comparison with 1A*) demonstrate the rate accelerating effects of sodium acetate. In Example 1 a 16.7% reduction in cycle time is achieved with the use of NaOAc. In Example 2 there is shown a leveling effect when the amount of NaOAc is doubled.

thiourea (TU) on both reaction rate and the precipitate formation.

COMPARATIVE EXAMPLE NO. 3I* and EXAMPLE NO. 3, COMPARATIVE EXAMPLE NO. 4A* and EXAMPLE NO. 4, COMPARATIVE EXAMPLE NO. 5A* and EXAMPLE NO. 5, and COMPARATIVE EXAMPLE NO. 6A* and EXAMPLE NO. 6

These eight procedures or four pairs of experiments are conducted using four different lots of commercially available, industrial grade NaSCN solution in which impurities such $NH_4SCN$ and thiourea are known to be present in varying amounts. The reaction times for Comparative Example Nos. 3I*, 4A*, 5A*, and 6A* vary from 9½ to 10 hrs. In addition, heavy precipitate formation is observed. However, when sodium acetate is added to the reaction, in accordance with the present invention, in Example Nos. 3, 4, 5, and 6, the reaction time is reduced to 7.25 to 8.0 hrs. with a resultant reduction in manufacturing vessel usage of 15.8%, Example No. 3, to 23.7%, Example No. 5. At the same time only a moderate precipitate formation is observed with use of sodium acetate co-catalyst.

EXAMPLES NOS. 7, 8, and 9

Using the same lot of industrial grade NaSCN as Example No. 4), the co-catalytic effects of a trisodium phosphate salt, Example No. 7, of a sodium tetraborate, Example No. 8, and of a sodium salt of carbonic acid, Example No. 9, are evaluated. All three procedures show that the adverse effects of thiourea and NH4SCN on reaction rate are essentially eliminated. Furthermore, the observed precipitation formation is only slight.

EXAMPLE 10

The procedure of Example 1 is again followed except that the quinoline is replaced by pyridine. Substantially the same results are obtained.

EXAMPLE 11

Commercial grade quinoline which contains about 5% isoquinoline is used in place of the pure quinoline of Example 1. Similar results are obtained.

EXAMPLES 12-14

The procedure of Example 1 is again followed except that the catalysts are varied. Instead of quinoline, the following are used: 6-methoxyquinoline, 6-chloroquinoline, and 4-chloropyridine. Substantially the same results are obtained.

EXAMPLE 15

The procedure of Example 1 is again followed except that potassium thiocyanate solution (50%) is used. Substantially the same results are obtained.

EXAMPLE 16

Again following the procedure of Example 1, sodium thiocyanate solution (50%) is reacted with 2-ethylhexylchloroformate. The resultant 2-ethylhexylcarbonyl isothiocyanate is recovered with no substantial precipitate formation.

EXAMPLE 17

Following the procedure of Example 16, n-octyl chloroformate is used in place of the 2-ethylhexylchloroformate, all else remaining equal. An excellent yield of n-octylcarbonyl isothiocyanate is recovered, with no precipitate formation.

EXAMPLE 18

Again following the procedure of Example 16 except that ethyl bromoformate is employed, similar results are achieved.

EXAMPLE 19

To 162 Parts of a 50% aqueous sodium thiocyanate solution are added 2.0 parts of quinoline and 2.8 parts of sodium acetate. With stirring, the mixture is cooled to 8° C. with ice/water. Phenylchloroformate (78.3 parts) is introduced dropwise in 1½ hours. The reaction is carried out at 10° C., and monitored for completeness by GC. The product, phenoxycarbonyl isothiocyanate is recovered in good yield and with only a slight precipitate formation.

EXAMPLE 20

The procedure of Example 19 is repeated substituting for the phenylchloroformate 60.3 parts of allychloroformate. Allyloxycarbonyl isothiocyanate is produced in good yield. Similar results are achieved.

The above-mentioned patents, any application(s), and publications are incorporated herein by reference.

Many variations in the present invention will suggest themselves to those skilled on this are in light of the above, detailed description. All such obvious variations are within the full intended scope of the appended claims.

What is claimed is:

1. A process for the production of a alkoxy or aryloxy isothiocyanate which comprises contacting a haloformate having the formula

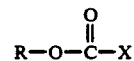

wherein R is an alkyl radical, an alkene radical, or an aryl radical and X is a halogen, with an alkali or alkaline earth metal thiocyanate under an appropriate rate of addition of haloformate such as to prevent a run-away reaction, in the presence of water,
   (i) from about 0.1% to about 10.0% by weight, based on the weight of haloformate, of a catalyst comprising a six membered mononuclear or ten membered fused polynuclear aromatic, heterocyclic compound having 1 or 2 nitrogen atoms as the only hetero atoms in the ring; and
   (ii) from about 0.1% to about 15.0% by weight, based on the weight of thiocyanate of a co-catalyst comprising an alkali metal or alkaline earth metal salt of an acid having a pKa of about $10^{-3}$ or below,
and at a temperature ranging from about $-10°$ C. to about 40° C. for up to about 16 hours.

2. A process according to claim 1 wherein R is an ethyl radical.

3. A process according to claim 1 wherein R is a phenyl radical.

4. A process according to claim 1 wherein the haloformate is ethyl chloroformate.

5. A process according to claim 1 wherein the alkali metal thiocyanate is sodium thiocyanate.

6. A process according to claim 1 wherein the catalyst comprises a pyridine or a quinoline compound unsubstituted in the 2-position.

7. A process according to claim 1 wherein the catalyst is pyridine.

8. A process according to claim 1 wherein the catalyst is quinoline.

9. A process according to claim 1 wherein the co-catalyst is a sodium or potassium salt of a substituted or unsubstituted saturated or unsaturated carboxylic acid, a substituted or unsubstituted aromatic acid, carbonic acid, boric acid, phosphoric acid, or a mixture of any of the foregoing.

10. A process according to claim 9 wherein the co-catalyst is selected from sodium acetate, sodium phosphate, sodium borate, sodium carbonate, or a mixture of any of the foregoing.

11. A process according to claim 1 wherein R is ethyl, X is chlorine, the alkali metal thiocyanate is sodium thiocyanate, the catalyst is quinoline, and the co-catalyst is sodium acetate.

* * * * *